United States Patent [19]
Breton et al.

[11] Patent Number: 6,147,121
[45] Date of Patent: *Nov. 14, 2000

[54] SKIN TONING BY STIMULATING COLLAGEN SYNTHESIS/PROLIFERATION OF DERMAL FIBROBLASTS

[75] Inventors: Lionel Breton, Versailles; Christel Liviero; Dominique Fagot, both of Paris, all of France

[73] Assignee: Societe L'Oreal S.A., Paris, France

[*] Notice: This patent is subject to a terminal disclaimer.

[21] Appl. No.: 09/288,624

[22] Filed: Apr. 9, 1999

[30] Foreign Application Priority Data

Apr. 10, 1998 [FR] France ................... 98 04571

[51] Int. Cl.$^7$ ............................................. A61K 31/065
[52] U.S. Cl. .................................................. 514/726
[58] Field of Search ........................... 424/401, 403; 514/77, 8, 646, 726, 738, 739

[56] References Cited

U.S. PATENT DOCUMENTS

| | | | |
|---|---|---|---|
| 5,430,062 | 7/1995 | Cushman et al. | 514/646 |
| 5,616,332 | 4/1997 | Herstein | 424/401 |
| 5,652,228 | 7/1997 | Bissett | 514/77 |
| 5,723,291 | 3/1998 | Kushner et al. | |
| 5,780,042 | 7/1998 | Gers-Barlag et al. | 424/401 |
| 5,837,224 | 11/1998 | Voorhees et al. | 424/59 |
| 5,840,681 | 11/1998 | Hersh et al. | 514/8 |
| 5,869,068 | 2/1999 | Lacharriere et al. | 424/401 |

FOREIGN PATENT DOCUMENTS

| | | | |
|---|---|---|---|
| 773020 | 5/1997 | European Pat. Off. | A61K 7/48 |
| 904774 | 9/1997 | European Pat. Off. | A61K 7/48 |
| 08175960A | 7/1996 | Japan | A61K 7/48 |
| WO 99/03816 | 1/1999 | WIPO . | |

OTHER PUBLICATIONS

Vaillant et al., Skin and esthetic alterations in menopause, Reproduction Humaine et Hormones, vol. 8/4, pp. 203–208, 1995.

Chen et al., Suppression of extracellular ATP . . . , Journal of Neurochemistry, vol. 69, p. S37, (1997).

Daphna–Iken et al., interleukin–1.beta. induces interstitial collagenase . . . , American J. of Physiology, vol. 369/6 pp. (F831–F837), (1995).

Moebius W., The modern treatment of menopausal complaints, Zeitschrift fur Arztliche fortbildung, vol. 68/15, pp. 796–801, (1974).

Patent Abstracts of Japan, vol. 96, No. 011, Nov. 29, 1996.

Database WPI, Week 10/98, Derwent Publications Ltd., Londo, GB; AN 98–105073 XP002095188.

Chemical Abstracts, vol. 128, No. 13, Mar. 30, 1998, Abstract No. 158748, XP002093496.

Chemical Abstracts, vol. 87, No. 3, Jul. 18, 1997, Abstract No. 16441, XP002093497.

Patent Abstracts of Japan, vol. 098, No. 4, Mar. 31, 1998, Pub. No. 09 328410 A.

Bombardelli et al., Fitoterapia, vol. 66, No. 4, 1995, pp. 291–317, XP002095075.

Patent Abstracts of Japan, vol. 15, No. 297, Publication No. 03109343, Sep. 5, 1991.

Japanese Patent Application First Publication No. Sho 64–38009, Laid open date: Feb. 8, 1989.

Japanese Patent Application First Publication No. Hei 08–175960, Publication Date: Jul. 9, 1996.

Patent Abstracts of Japan, Publ. No. 09241617, Sep. 16, 1997.

Patent Abstracts of Japan, Publ. No. 09328410, Dec. 22, 1997.

*Primary Examiner*—William R. A. Jarvis
*Assistant Examiner*—Vickie Kim
*Attorney, Agent, or Firm*—Burns, Doane, Swecker & Mathis, L.L.P.

[57] ABSTRACT

The hydroxystilbenes are effective collagen-synthesizing, and/or fibroblast-proliferating, and/or protease expression-inhibiting, and/or skin aging-combating, and/or flaccid/wrinkled skin-treating, and/or skin-smoothing/firming, and/or menopausal cutaneous effect-treating, and/or menopausal collagen/fibroblast effects-treating active agents, for topical application onto the skin and/or mucous membranes of a human subject in need of such treatment(s).

14 Claims, No Drawings

SKIN TONING BY STIMULATING COLLAGEN SYNTHESIS/PROLIFERATION OF DERMAL FIBROBLASTS

CROSS-REFERENCE TO PRIORITY APPLICATION

This application claims priority under 35 U.S.C. §119 of FR-98/04571, filed Apr. 10, 1998 and hereby expressly incorporated by reference.

CROSS-REFERENCE TO COMPANION APPLICATIONS

Copending applications Ser. No. 09/288,626 [Attorney Docket No. 016800-283], and Ser. No. 09/284,625 [Attorney Docket No. 016800-284], both filed concurrently herewith and both assigned to the assignee hereof.

BACKGROUND OF THE INVENTION

1. Technical Field of the Invention

The present invention relates to promoting the toning of human skin by stimulating, via topical application thereto of at least one hydroxystilbene compound, the restructuring of the skin and/or mucous membranes, whether by stimulating the synthesis of collagen and/or stimulating the proliferation of the fibroblasts of the dermis.

This invention also relates to skin-toning compositions comprising at least one hydroxystilbene compound.

2. Description of the Prior Art

Human skin consists of two layers, namely, a superficial or upper layer, the epidermis, and a deep layer, the dermis.

The natural human epidermis is principally composed of three types of cells which are the keratinocytes, highly predominant, the melanocytes and the Langerhans' cells. Each of these cell types contributes, through its specific functions, to the essential role played by the skin.

The dermis provides a solid support for the epidermis. It is also its feeder layer. It consists mainly of fibroblasts and an extracellular matrix itself composed of various extracellular proteins, including among which are, in particular, collagen fibers, elastin and various glycoproteins. All of these extracellular species are synthesized by the fibroblast. Also present in the dermis are leukocytes, mastocytes or tissue macrophages. Finally, the dermis contains blood vessels and nerve fibers.

The fibroblast, by virtue of its activity in the synthesis of extracellular matrix proteins (proteoglycans, collagen fibers and other structural glycoproteins) is the primary constituent in the structural assembly of the dermis.

The collagen fibers are responsible for the solidity of the dermis. These are very resistant but sensitive to certain enzymes generally deemed collagenases. In the dermis, the collagen fibers consist of fibrils firmly attached to each other, thus forming more than ten types of different structures. The structure of the dermis is in large part due to the entanglement of the packed collagen fibers. The collagen fibers participate in the tonicity of the skin.

The collagen fibers are regularly renewed but this renewal decreases with age, which causes, in particular, a reduction in the thickness of the dermis.

It is also accepted that extrinsic factors such as ultraviolet radiation or tobacco smoke also have an adverse effect on the skin and on its collagen level.

However, various factors cause the degradation of collagen, with all the consequences which can be expected on the structure and/or firmness of the skin and/or mucous membranes.

Although very resistant, the collagen fibers are sensitive to certain enzymes, the collagenases. Degradation of the collagen fibers causes the appearance of flabby and wrinkled skin which humans, preferring the appearance of a smooth and firm skin, have always sought to combat.

Collagenases belong to the family of enzymes denominated metalloproteinases (MMPS) which are themselves members of a family of proteolytic enzymes (endoproteases) which contain a zinc atom coordinated with three cysteine residues and a methionine species in their active site and which degrade the macromolecular components of the extracellular matrix and the basal sheets at neutral pH (collagen, elastin, and the like).

Being very widely distributed in the human body, these enzymes are present, but weakly expressed, in normal physiological phenomena such as organ growth and tissue renewal.

The metalloproteinase family consists of several well-defined groups based on their resemblance in terms of structure and substrate specificity (see Woessner J. F., *Faseb Journal*, vol. 5, 2145 (1991)). Among these groups, exemplary are the collagenases intended for degrading fibrillar collagens (MMP-1 or interstitial collagenase, MMP-8 or neutrophil collagenase, MMP-13 or collagenase 3), gelatinases which degrade collagen type IV or any form of denatured collagen (MMP-2 or gelatinase A (72 kDa), MMP-9 or gelatinase B (92 kDa)) stromelysins (MMP-3) whose broad activity spectrum applies to extracellular matrix proteins such as glycoproteins (fibronectin, laminin), proteoglycans, and the like, or, alternatively, membrane metalloproteinases. Prolonged exposure to ultraviolet radiation, particularly to UV-A and/or UV-B ultraviolet radiation, elicits the effect of stimulating the expression of collagenases, particularly of MMP-1. This constitutes one of the components of photoinduced skin aging.

Moreover, at menopause, the principal modifications regarding the dermis are a reduction in the collagen level and in the dermal thickness. This causes, in menopausal women, a reduction in the thickness of the skin. Women then experience a sensation of "dry skin" or of tight skin and a marked increase in surface fine lines and fine wrinkles is observed. The skin exhibits a rough appearance upon palpation. Finally, the skin exhibits a reduced suppleness.

It too is known that women gradually lose their collagen level yearly after menopause and that 30% of the overall level is lost in the first five years postmenopause.

The importance of the presence of collagen fibers in the skin and the importance of maintaining, or even increasing, the amount thereof, thus, are self-evident.

Serious need therefore continues to exist for active species/agents that maintain the level of collagen in the skin and maintain a smooth and firm appearance thereof.

SUMMARY OF THE INVENTION

It has now surprisingly and unexpectedly been determined that the hydroxystilbenes elicit the responses of stimulating the synthesis of collagen and/or of stimulating the proliferation of the fibroblasts of the dermis and/or of inhibiting the expression of proteases of the extracellular matrix, particularly metalloproteinases and, even more particularly, type 1 metalloproteinase.

The hydroxystilbenes according to the present invention advantageously are compounds having the following structural formula (I):

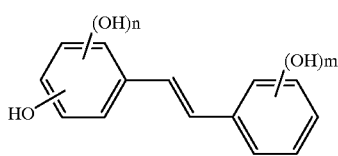

(I)

in which n is an integer ranging from 0 to 4, inclusive, and m is an integer ranging from 0 to 5, inclusive. These compounds may be in a cis- or transconfiguration.

According to the invention, by the term hydroxystilbene are intended both the compounds of formula (I) and the hydroxyalkylated derivatives thereof.

DETAILED DESCRIPTION OF BEST MODE AND SPECIFIC/PREFERRED EMBODIMENTS OF THE INVENTION

More particularly according to the present invention, the hydroxystilbenes are compounds which exist in the natural state in plants of the class of spermatophytes and particularly in grapevines. Such compounds as, for example resveratrol, are found in grapes and in wine.

In the prior art, the hydroxystilbenes are used, inter alia, as depigmenting agents (JP-87/192040), as vasodilating agents (EP-96/830517), as antithrombotic agents (JP-05/016413), in the treatment of various cardiovascular conditions (CA 2187990), as mutagenesis and carcinogenesis inhibiting agents (JP-06/024967), or, alternatively, are described as antioxidants.

Among these compounds, resveratrol (or 3,4',5-trihydroxystilbene) is of particular interest for the activities described above mainly because it is a natural compound which is found in grape skins and in wine. In this regard, the review by Soleas et al., *Clinical Biochemistry*, Vol. 30, No. 2, pp. 91–113 (1997) perfectly summarizes the state of the art respecting this compound and the hydroxystilbenes generically.

However, to date the capacity of the hydroxystilbenes to stimulate the synthesis of collagen and/or the proliferation of the fibroblasts of the dermis and/or the inhibition of the expression of proteases of the extracellular matrix was unknown.

The present invention therefore features the use of an effective amount of at least one hydroxystilbene, or composition comprised thereof, to stimulate the synthesis of collagen and/or the proliferation of the fibroblasts of the dermis and/or to inhibit the expression of proteases of the extracellular matrix, particularly metalloproteinases and even more particularly type 1 metalloproteinase.

Among the hydroxystilbenes, particularly representative are the mono-, di-, tri-, tetra-, penta-, hexa-, hepta-, octo- or nonahydroxystilbenes, as well as the hydroxyalkylated derivatives thereof.

According to the invention, the hydroxystilbenes may be used either alone or in the form of mixtures of any type and may be natural or synthetic in origin.

Advantageously the hydroxystilbenes according to the invention are selected from among:
4'-hydroxystilbene,
2',4'-dihydroxystilbene,
3',4'-dihydroxystilbene,
4,4'-dihydroxystilbene,
2',4,4-trihydroxystilbene,
3',4',4-trihydroxystilbene,
2,4,4'-trihydroxystilbene,
3,4,4'-trihydroxystilbene,
3,4',5-trihydroxystilbene,
2',3,4-trihydroxystilbene,
2,3',4-trihydroxystilbene,
2',2,4'-trihydroxystilbene,
2,4,4',5-tetrahydroxystilbene,
2',3,4',5-tetrahydroxystilbene,
2,2',4,4'-tetrahydroxystilbene,
3,3',4',5-tetrahydroxystilbene,
2,3',4,4'-tetrahydroxystilbene,
3,3',4,4'-tetrahydroxystilbene,
3,3',4',5,5'-pentahydroxystilbene,
2,2',4,4',6-pentahydroxystilbene,
2,3',4,4',6-pentahydroxystilbene,
2,2',4,4',6,6'-hexahydroxystilbene.

3,4',5-Trihydroxystilbene (or resveratrol) is the preferred compound according to the invention.

Per this invention, a hydroxystilbene or composition comprised thereof is topically applied onto the skin to elicit the desired therapeutic/cosmetic response.

As indicated above, collagen is implicated in the solidity of the dermis, and therefore in the firmness of the skin and/or mucous membranes and the fibroblasts are responsible for the synthesis of the proteins of the extracellular matrix of the dermis, especially collagen.

Thus, this invention features the use of an effective amount of at least one hydroxystilbene or composition comprised thereof to treat, preventively or curatively, the cutaneous signs of aging, more particularly to treat, preventively or curatively, flaccid and/or wrinkled skin.

Indeed the hydroxystilbene or composition comprised thereof is topically applied to reduce the cutaneous signs of aging, more particularly to reduce the appearance of flaccid and/or wrinkled skin.

Thus, this invention also features the use of an effective amount of at least one hydroxystilbene or composition comprised thereof to stimulate the toning of the skin.

Too, the present invention features the use of an effective amount of at least one hydroxystilbene or composition comprised thereof to promote the smoothing of the skin and/or to firm the skin.

This invention likewise features the use of an effective amount of at least one hydroxystilbene or composition comprised thereof to combat the cutaneous effects of menopause, more particularly the effects of menopause on collagen and/or the fibroblasts.

The amount of hydroxystilbene administered according to the invention quite obviously depends on the desired effect and should be an amount which is effective to stimulate the synthesis of collagen and/or the proliferation of the fibroblasts of the dermis and/or to inhibit the expression of proteases of the extracellular matrix.

For example, the amount of hydroxystilbene administered according to the invention advantageously ranges from 0.001% to 10% and preferably from 0.005% to 5% of the total weight of the composition.

The subject compositions are preferably cosmetic or dermatological, advantageously cosmetic compositions.

The present invention thus features cosmetic compositions to treat, preventively or curatively, the cutaneous signs of aging, more particularly to treat, preventively or curatively, flaccid and/or wrinkled skin, comprising, in a cosmetically acceptable medium (vehicle, diluent or carrier) an effective amount of at least one hydroxystilbene.

Preferably, such compositions are topically applied to reduce the cutaneous signs of aging, more particularly to reduce the appearance of flaccid and/or wrinkled skin.

Also featured hereby are toning cosmetic compositions comprising, in a cosmetically acceptable medium, an effective amount of at least one hydroxystilbene.

The subject cosmetic compositions are also useful for smoothing the skin.

The subject cosmetic hydroxystilbene compositions are also useful for stimulating the synthesis of collagen and/or the proliferation of the fibroblasts of the dermis and/or for inhibiting the expression of proteases of the extracellular matrix.

And the subject cosmetic compositions too are useful for combating the cutaneous effects of menopause, more particularly the effects of menopause on collagen and/or the fibroblasts.

By "cosmetically acceptable medium" is intended a vehicle, diluent or carrier which is compatible with the skin, the mucous membranes, the nails and the hair.

The compositions according to the invention comprise a cosmetically acceptable vehicle, diluent or carrier and may be formulated in all the dosage forms normally employed for topical application, in particular in the form of an aqueous, aqueous/alcoholic or oily solution, an oil-in-water or water-in-oil or multiple emulsion, an aqueous or oily gel, an anhydrous liquid, a pasty or solid product, a dispersion of oil in an aqueous phase with the aid of spherules, it being possible for these spherules to be polymeric nanoparticles such as nanospheres and nanocapsules or more preferably lipid vesicles of the ionic and/or nonionic type.

The subject compositions may be fluid to a greater or lesser degree and may have the appearance of a white or colored cream, an ointment, a milk, a lotion, a serum, a paste, a foam, etc. Such compositions may optionally be applied to the skin in the form of an aerosol. They may also be provided in solid form, for example in the form of a stick. They may be used as a treatment product, as a cleansing product, as a makeup product or, alternatively, as a simple deodorant product.

In known manner, the compositions of the invention may also contain the customary additives and adjuvants in the cosmetic and dermatological fields, such as hydrophilic or lipophilic gelling agents, hydrophilic or lipophilic active agents, preservatives, antioxidants, solvents, perfumes, fillers, UV-screening agents, pigments, chelating agents, odor absorbers and colorants. The amounts of these various additives and adjuvants are those conventional in the fields under consideration, and range for example, from 0.01% to 20% of the total weight of the composition. These additives and adjuvants, depending on their nature, may be introduced into the fatty phase, into the aqueous phase, into the lipid vesicles and/or into the nanoparticles.

When a composition of the invention is an emulsion, the proportion of the fatty phase may range from 5% to 80% by weight, and preferably from 5% to 50% of the total weight of the composition. The oils, the emulsifiers and the coemulsifiers included in the composition in the form of an emulsion are selected from among those conventional to the particular field. The emulsifier and the coemulsifier are advantageously present in the composition in a proportion ranging from 0.3% to 30% by weight, and preferably from 0.5% to 20% of the total weight of the composition.

Exemplary oils according to this invention include the mineral oils, oils of plant origin (apricot oil, sunflower oil), oils of animal origin, synthetic oils, silicone oils and fluorinated oils (perfluoropolyethers). Also exemplary are fats, fatty alcohols (cetyl alcohol), fatty acids, waxes (beeswax).

Exemplary emulsifiers and coemulsifiers include esters of fatty acid and polyethylene glycol such as PEG-40 stearate, PEG-100 stearate, esters of fatty acid and polyol such as glyceryl stearate and sorbitan tristearate.

And exemplary hydrophilic gelling agents, include, in particular, carboxyvinyl polymers (carbomer), acrylic copolymers such as copolymers of acrylates/alkyl acrylates, polyacrylamides, polysaccharides, natural gums and clays, and exemplary lipophilic gelling agents, modified clays such as bentones, metal salts of fatty acids, hydrophobic silica and polyethylenes.

The subject compositions may contain other hydrophilic active agents such as proteins or protein hydrolysates, amino acids, polyols, urea, allantoin, sugars and sugar derivatives, water-soluble vitamins, plant extracts and hydroxy acids.

Representative such lipophilic active agents include retinol (vitamin A) and derivatives thereof, tocopherol (vitamin E) and derivatives thereof, essential fatty acids, ceramides, essential oils, salicylic acid and derivatives thereof.

Advantageously employed in combination with the hydroxystilbene according to the invention are:

(a) plant hormones;

(b) scavengers of OH radicals, such as dimethyl sulfoxide;

(c) chlorine channel openers;

(d) vegetable extracts such as those of Iridaceae, Rosaceae or soya bean, which extracts may then contain isoflavones or otherwise;

(e) extracts of microorganisms, including, in particular bacterial, extracts such as those of nonphotosynthetic filamentous bacteria.

Other compounds and active agents may also be added, for example phospholipids such as lecithin, linoleic and linolenic acids, salicylic acid and derivatives thereof described in FR-2,581,542, such as the salicylic acid derivatives bearing an alkanoyl group having from 2 to 12 carbon atoms at the 5-position of the benzene ring, hydroxycarboxylic or ketocarboxylic acids and esters thereof, lactones and their corresponding salts, carotenoids, eicosatetraenoic and eicosatrienoic acids or their esters and amides, vitamin E and derivatives thereof.

In one embodiment of the invention, at least one hydroxystilbene may, inter alia, be administered together with other active agents intended especially for the prevention and/or treatment of skin conditions. Among such active agents, representative are:

(f) agents modulating pigmentation such as kojic acid or hydroquinone;

(g) agents modulating bacterial adhesion to the skin and/or mucous membranes such as honey, especially honey derived from acacias and certain sugar derivatives;

(h) keratolytic agents such as alpha- and beta-hydroxycarboxylic or beta-ketocarboxylic acids, their salts, amides or esters and more particularly hydroxy acids such as glycolic acid, lactic acid, salicylic acid, citric acid and, in general, fruit acids and 5-n-octanoylsalicylic acid;

(i) anti-free radical agents, such as alphatocopherol and its esters, superoxide dismutases, certain metal chelators or ascorbic acid and its esters;

(j) antidandruff agents such as octopirox or zinc pyrithione;

(k) anti-acne agents such as benzoyl peroxide;

(l) substances such as substance P, CGRP or bradykinin antagonists or NO synthase inhibitors or, alternatively, sodium channel inhibitors, compounds described as being active in the treatment of sensitive skins and as having anti-irritant effects, in particular vis-à-vis irritant compounds which may be present in the compositions.

Also exemplary of the additive/adjuvant active agents, are, in particular, moisturizers such as polyols (for example glycerin), vitamins (for example D-panthenol), soothing agents (allantoin, cornflower water), UVA- and UVB-screening agents, matting agents (for example partially crosslinked polydimethylorganosiloxanes marketed under the trademark KSG® by Shin Etsu), and mixtures thereof.

It is also intended to include antiwrinkle active agents and in particular toning products such as vegetable proteins and their hydrolysates, in particular the extract of soya bean proteins marketed under the trademark Eleseryl® by LSN or the oats derivative marketed under the trademark Reductine® by Silab.

As the skin contains many other components other than collagen and the fibroblasts, it is advantageous, when a hydroxystilbene according to the invention is administered, to promote at the same time the synthesis of these other components such as, for example, lipids and/or to promote the proliferation of other cellular components such as, for example, the keratinocyt Thus, this invention also features cosmetic compositions comprising, in a cosmetically acceptable medium, at least one hydroxystilbene and at least one other active agent stimulating the synthesis of lipids and/or the proliferation of keratinocytes.

In this regard, exemplary active agents stimulating the synthesis of lipids are plant hormones, such as auxins, or compounds of plant origin, such as cinnamic acid, and exemplary active agent stimulating proliferation of keratinocytes are compounds of plant origin, such as phloroglucinol.

Accordingly, the compositions of this invention may also comprise hydroxystilbene, cinnamic acid or derivatives thereof and/or a plant hormone, in particular an auxin chosen from among indoleacetic acid (IAA), 4-chloroindole-3-acetic acid (4-CI-IAA), phenylacetic acid (PAA), indole-3-butyric acid (IBA), 2,4-dichlorophenoxyacetic acid (2,4-D), α-naphthaleneacetic acid (α-NAA), β-naphthoxyacetic acid, indoleethanol, idoleacetaldehyde and indoleacetonitrile and/or a plant compound such as phloroglucinol.

Too, the hydroxystilbenes may be formulated into cosmetic and/or pharmaceutical, particularly dermatological, compositions suited to stimulate the synthesis of collagen and/or the proliferation of the fibroblasts of the dermis.

In order to further illustrate the present invention and the advantages thereof, the following specific examples are given, it being understood that same are intended only as illustrative and in nowise limitative.

In said examples to follow, all parts and percentages are given by weight, unless otherwise indicated.

EXAMPLE 1

Investigating the effect of resveratrol on the synthesis of collagen:

This study was carried out by measuring the incorporation of radioactive proline into the proteins newly synthesized by normal human dermal fibroblast cultures. These newly synthesized proteins were predominantly collagen fibers.

The fibroblast cultures were conducted according to conventional cell culture techniques, namely, in MEM/M199 medium marketed by Gibco, in the presence of sodium bicarbonate (1.87 mg/ml), of L-glutamine (2 mM), of penicillin (50 IU/ml) and of 10% fetal calf serum (Gibco).

The test was carried out on 80% confluent cell cultures in a 24-well plate. Resveratrol, at the concentration of $10^{-4}$ M, was placed in contact with the cells for 48 hours. The labelling with tritiated proline (L-[2,3-$^3$H]proline marketed by Amersham, 33 mCi/ml) was conducted for 24 hours. The amount of tritiated proline incorporated was measured at the end of the test by acid precipitation of the proteins on filters and liquid scintillation counting.

The results were evaluated relative to a control consisting of cells which were not treated with resveratrol.

A positive control (vitamin C at 20 mg/ml) known to stimulate the synthesis of collagen was included in the test as a reference.

The results of this test are reported in the following Table I.

TABLE I

| Treatment | cpm | s.d. | % | p |
|---|---|---|---|---|
| Not treated | 22,528 | 1918 | 100 | — |
| Resveratrol 1.25 mM | 27,164 | 502 | 121 | <0.01 |
| Resveratrol 5.00 mM | 25,769 | 1112 | 114 | <0.05 |
| Vitamin C (control) | 36,431 | 417 | 162 | <0.01 | cpm: counts per minute.
s.d.: standard deviation.
p: confidence interval calculated according to the Dunett method.

These results evidenced that resveratrol substantially stimulated the incorporation of proline into collagen and that it therefore activated the neosynthesis of proteins, especially collagen.

EXAMPLE 2

Investigating the effect of resveratrol on the proliferation of the fibroblasts of the dermis:

This study was carried out by measuring the incorporation of radioactive thymidine into normal human dermal fibroblast cultures.

The fibroblast cultures were conducted according to conventional cell culture techniques, namely in MEM/M199 medium marketed by Gibco, in the presence of sodium bicarbonate (1.87 mg/ml), of L-glutamine (2 mM), of penicillin (50 IU/ml) and of 10% fetal calf serum (Gibco).

The test was carried out on 80% confluent cell cultures in a 24-well plate. Resveratrol, at the concentration of 1.25 mM and 5 mM, was placed in contact with the cells for 48 hours. The labelling with tritiated thymidine ([methyl-$^3$H] thymidine marketed by Amersham, 82 Ci/mmol) was conducted for 24 hours.

The amount of tritiated thymidine incorporated was measured at the end of the test by acid precipitation of the proteins on filters and liquid scintillation counting.

The results were evaluated relative to a control consisting of cells which were not treated with resveratrol.

A positive control (fetal calf serum at 20%) known to stimulate the synthesis of collagen was included in the test as a reference.

The results of this test are reported in the following Table II:

TABLE II

| Treatment | cpm | s.d. | % | p |
|---|---|---|---|---|
| Not treated | 13,649 | 1076 | 100 | — |
| Resveratrol 1.25 mM | 15,055 | 831 | 110 | <0.05 |
| Resveratrol 5.00 mM | 19,229 | 1407 | 141 | <0.01 |
| FCS 20% (control) | 17,186 | 1426 | 126 | <0.05 | cpm: counts per minute.
s.d.: standard deviation.
p: confidence interval calculated according to the Dunett method.

EXAMPLE 3

Effect of resveratrol on the expression of the collagenases:

The effect of resveratrol on the production of interstitial collagenase was evaluated in a model of culture of A2058 cells (derived from human malanomas: Templeton N. S. et al., *Cancer Res.*, SO.- 54315431(1990)).

The cells were incubated in a phenol red-free MEM medium containing amino acids at the concentration of 2 mM, sodium pyruvate at the concentration of 1 mM and 10% charcoal-treated calf serum. They were then cultured at the density of 20,000 cells per well in the 24 wells of a multiwell plate.

Twenty-four hours after cultering, the cells were contacted with resveratrol. The production of interstitial collagenase was evaluated 96 hours later in the culture medium. This was carried out with the aid of an Elisa kit (Biotrack human MMPL; Amersham).

The resveratrol was tested at the concentrations $2 \times 10^{-7}$ M and $2 \times 10^{-6}$ M.

The results, expressed as percentages, represent the reduction in the production of interstitial collagenase compared with the control, namely, compared with a culture carried out under the same conditions in the absence of resveratrol.

The results obtained are reported in the following Table III:

TABLE III

|  | Resveratrol 0.2 μM | Resveratrol 2 μM |
|---|---|---|
| % inhibition | 14% | 57% |

The results evidenced that resveratrol reduced the production of interstitial collegenase by the A 2058 cells and this in a dose-dependent manner.

EXAMPLE 4

Examples of specific compositions according to the invention: these compositions were formulated via the usual techniques commonly employed in the cosmetic or pharmaceutical fields:

| Composition 1: Treatment cream | |
|---|---|
| Beeswax | 1.50% |
| Apricot stone oil | 13.00% |
| Perfume | 0.40% |
| Resveratrol | 1.00% |
| Xanthan | 0.50% |
| Cyclopentadimethylsiloxane | 5.00% |
| Sucrose mono-di-palmitostearate | 3.00% |
| Methylglucose sesquistearate | 3.00% |
| Stearic acid | 1.00% |
| Cetyl alcohol | 3.00% |
| Preservatives | 0.30% |
| Sterilized demineralized water | qs 100.00% |
| Composition 2: Body oil | |
| Liquid petroleum jelly | 47.99% |
| Apricot stone oil | 6.00% |
| Perfume | 1.00% |
| Resveratrol | 0.50% |
| Cyclopentadimethylsiloxane | 45.00% |
| Composition 3: Makeup removing milk | |
| 2-Ethylhexyl palmitate | 10.50% |
| Liquid fraction of shea butter | 16.50% |
| Preservatives | 0.30% |
| Perfume | 0.15% |

| -continued | |
|---|---|
| Resveratrol | 0.10% |
| Sodium hydroxide | 0.04% |
| Carboxyvinyl polymer | 0.20% |
| Sterilized demineralized water | 69.80% |
| Mixture of cetylstearylglucoside and of cetyl and stearyl alcohols | 2.50% |
| Composition 4: Treatment cream | |
| Beeswax | 1.50% |
| Apricot stone oil | 13.00% |
| Preservatives | 0.30% |
| Perfume | 0.40% |
| Triethanolamine | 0.17% |
| Resveratrol | 1.50% |
| Beta-naphthoxyacetic acid | 0.01% |
| 2,4-Dichlorophenoxyacetic acid | 0.01% |
| Xanthan | 0.50% |
| Cyclopentadimethylsiloxane | 5.00% |
| Sucrose mono-di-palmitostearate | 3.00% |
| Methylglucose sesquistearate | 3.00% |
| Stearic acid | 1.00% |
| Cetyl alcohol | 3.00% |
| Sterilized demineralized water | qs 100.00% |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A method for stimulating the synthesis of collagen in the skin of a human subject in need of such treatment, comprising topically applying to said skin, for such period of time as required to elicit the desired response, an effective collagen-synthesizing amount of at least one hydroxystilbene.

2. A method for stimulating the proliferation of fibroblasts in the skin of a human subject in need of such treatment, comprising topically applying to said skin, for such period of time as required to elicit the desired response, an effective fibroblast-proliferating amount of at least one hydroxystilbene.

3. A method for inhibiting the expression of proteases of the extracellular matrix in the skin of a human subject in need of such treatment, comprising topically applying to said skin, for such period of time as required to elicit the desired response, an effective protease expression-inhibiting amount of at least one hydroxystilbene.

4. The method as defined by claim 3, comprising topically applying to said skin, for such period of time as required to elicit the desired response, an effective metalloproteinase expression-inhibiting amount of at least one hydroxystilbene.

5. The method as defined by claim 4, comprising topically applying to said skin, for such period of time as required to elicit the desired response, an effective type 1 metalloproteinase expression-inhibiting amount of at least one hydroxystilbene.

6. A method for treating the cutaneous signs of aging of the skin of a human subject in need of such treatment, comprising topically applying to said skin, for such period of time as required to elicit the desired response, an effective amount of at least one hydroxystilbene to treat the cutaneous signs of skin aging.

7. A method for treating the flaccid and/or wrinkled skin of a human subject in need of such treatment, comprising topically applying to said skin, for such period of time as required to elicit the desired response, an amount of at least one hydroxystilbene effective to treat said flaccid and/or wrinkled skin.

8. A method for stimulating the toning of the skin of a human subject in need of such treatment, comprising topically applying to said skin, for such period of time as required to elicit the desired response, an effective skin-toning amount of at least one hydroxystilbene.

9. A method for promoting the smoothing and/or firming of the skin of a human subject in need of such treatment, comprising topically applying to said skin, for such period of time as required to elicit the desired response an effective skin-smoothing/firming amount of at least one hydroxystilbene.

10. A method for treating adverse cutaneous effects of menopause, comprising topically applying to the skin of a human subject in need of such treatment, for such period of time as required to elicit the desired response, an effective amount of at least one hydroxystilbene.

11. A method for treating adverse effects of menopause on the collagen and/or fibroblasts of the dermis of a human subject in need of such treatment, comprising topically applying to said skin, for such period of time as required to elicit the desired response, an effective amount of at least one hydroxystilbene.

12. The method as defined by any of claims 1, 2, 3, 6, 7, 8, 9, 10 or 11, said at least one hydroxystilbene having the structural formula (I), or hydroxyalkylated derivative thereof:

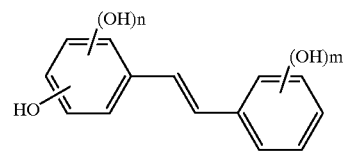

(I)

wherein n is integer ranging from 0 to 4 and m is an integer ranging from 0 to 5.

13. The method as defined by claim 12, said at least one hydroxystilbene being selected from the group consisting of 4'-hydroxystilbene, 2',4'-dihydroxystilbene, 3',4'-dihydroxystilbene, 4,4'-dihydroxystilbene, 2',4',4-trihydroxystilbene, 3',4',4-trihydroxystilbene, 2,4,4'-trihydroxystilbene, 3,4,4'-trihydroxystilbene, 3,4',5-trihydroxystilbene, 2',3,4-trihydroxystilbene, 2,3',4-trihydroxystilbene, 2',2,4'-trihydroxystilbene, 2,4,4',5-tetrahydroxystilbene, 2',3,4',5-tetrahydroxystilbene, 2,2',4,4'-tetrahydroxystilbene, 3,3',4',5-tetrahydroxystilbene, 2,3',4,4'-tetrahydroxystilbene, 3,3',4,4'-tetrahydroxystilbene, 3,3',4',5,5'-pentahydroxystilbene, 2,2',4,4',6-pentahydroxystilbene, 2,3',4,4',6-pentahydroxystilbene, and 2,2',4,4',6,6'-hexahydroxystilbene.

14. The method as defined by claim 13, said at least one hydroxystilbene comprising 3,4',5-trihydroxystilbene.

* * * * *